(12) United States Patent
Wieczorek et al.

(10) Patent No.: US 10,329,481 B2
(45) Date of Patent: Jun. 25, 2019

(54) USE OF 2-(4-STYRYLPHENYL)BENZOXAZOLE AND PLASTIC SCINTILLATOR

(71) Applicants: UNIWERSYTET JAGIELLONSKI, Cracow (PL); UNIWERSYTET ROLNICZY IM. HUGONA KOLLATAJA W KRAKOWIE, Cracow (PL)

(72) Inventors: Anna Wieczorek, Cracow (PL); Andrzej Danel, Cracow (PL); Tomasz Uchacz, Cracow (PL); Pawel Moskal, Cracow (PL)

(73) Assignees: UNIWERSYTET JAGIELLONSKI, Cracow (PL); UNIWERSYTET ROLNICZY IM. HUGONA KOLLATAJA W KRAKOWIE, Cracow (PL)

( * ) Notice: Subject to any disclaimer, the term of this patent is extended or adjusted under 35 U.S.C. 154(b) by 262 days.

(21) Appl. No.: 15/509,010

(22) PCT Filed: Jun. 8, 2015

(86) PCT No.: PCT/PL2015/050022
§ 371 (c)(1),
(2) Date: Mar. 6, 2017

(87) PCT Pub. No.: WO2016/036265
PCT Pub. Date: Mar. 10, 2016

(65) Prior Publication Data
US 2017/0260447 A1    Sep. 14, 2017

(30) Foreign Application Priority Data
Sep. 7, 2014   (PL) .......................... 409387

(51) Int. Cl.
| | | |
|---|---|---|
| *G21K 4/00* | (2006.01) | |
| *C09K 11/02* | (2006.01) | |
| *C09K 11/06* | (2006.01) | |
| *G01T 1/203* | (2006.01) | |
| *C07D 263/57* | (2006.01) | |

(52) U.S. Cl.
CPC ............ *C09K 11/06* (2013.01); *C07D 263/57* (2013.01); *C09K 11/025* (2013.01); *G01T 1/203* (2013.01); *G01T 1/2033* (2013.01); *G21K 4/00* (2013.01); *C09K 2211/1007* (2013.01); *C09K 2211/1033* (2013.01)

(58) Field of Classification Search
CPC . C09K 11/06; C09K 11/02; C09K 2211/1007; C09K 2211/1033; G01T 1/203; G01T 1/2033
See application file for complete search history.

(56) References Cited

U.S. PATENT DOCUMENTS 3,476,747 A * 11/1969 Young .................. C07C 2/84
548/152
2014/0027646 A1   1/2014  Zaitseva et al.

OTHER PUBLICATIONS

"Wieczorek et al., A pilot Study of the Novel J-PET Plastic Scintillator with 2-(4-styrylphenyl)benzoxazole as a Wavelnegth Shifter", Acta Physica Polonic A, vol. 127, No. 5, May 1, 2015, pp. 1487-1490.*
International Search Report and Written Opinion issued in corresponding International Patent Application No. PCT/PL2015/050022 dated Sep. 11, 2015 (8 pages).

* cited by examiner

*Primary Examiner* — C Melissa Koslow
(74) *Attorney, Agent, or Firm* — Kilyk & Bowersox, P.L.L.C.

(57) ABSTRACT

New composition of polymeric scintillator was revealed, which can be used particularly in medical diagnostics especially in productions of CT scanners, PET scanners and SPECT scanners.

3 Claims, 1 Drawing Sheet

USE OF 2-(4-STYRYLPHENYL)BENZOXAZOLE AND PLASTIC SCINTILLATOR

Figure 1:
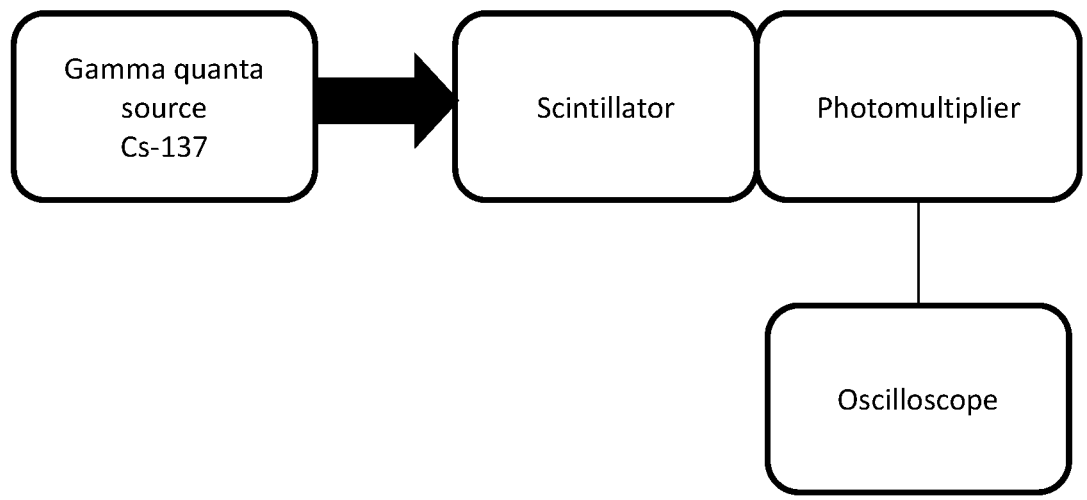

This application is a National Stage Application of PCT/PL2015/050022, filed Jun. 8, 2015, which claims priority to Polish Patent Application No. P.409387, filed Sep. 7, 2014, which are incorporated in their entireties by reference herein.

The subject of the invention is polymeric scintillator containing 2-(4-styrylphenyl)benzoxazole as the second fluorescent additive. The invitation can be used especially in the medical diagnostics, especially in productions of CT scanners, PET scanners and SPECT scanners.

Scintillators are commonly used detectors of not only gamma rays and X-rays but also charged and neutral particles. Scintillating materials can be divided in to two groups: organic and inorganic, and their properties depend on atomic number.

Scintillators are widely used in many fields of science and industry. They are the most common detectors used in particle physics and nuclear physics experiments, for example they are essential part of experimental systems installed in Large Hadron Collider in European Organization for Nuclear Research (CERN).

Scintillators are used also in astrophysics to observe new-forming stars, to search minerals and to conduct the security check at the airports as an alternative method for most often used X-rays during luggage scanning. On minefields scintillators help to localize explosives without risking human life.

Scintillators are also commonly used in nuclear medicine—medical diagnostics. They are the main part of scanners used for computer tomography (CT), positron emission tomography (PET) and single-photon emission computed tomography (SPECT). Those methods are based on detection of X-ray or gamma quanta which are the product of annihilation of electrons from body tissues with positions released by radio pharmaceutics given to the patient. Presently, annihilation gamma quanta are measured by scintillators built from inorganic crystals.

The meaning of the method PET and SPECT is growing because they are particularly effective in detecting more and more common cancers and also neurological, cardiac and gastronomical diseases.

Position emission tomography is one of the most advanced and noninvasive diagnostic techniques. In connection with growing demand for PET scanners, which number is insufficient in Poland and other countries, in two patent applications, WO2011/008118 and WO2011/008119, there was described an innovative method of construction of those devices.

The expensive inorganic scintillators are replaced by cheap polymeric scintillators. This solution creates new possibilities in the field of diagnostics, in enables examination of the patient simultaneously by two methods: position emission tomography (PET) and nuclear magnetic resonance (NMR) (patent application "Hybrid tomography scanner TOF-PET/MRI" No. P.405184 (2013), now issued as Polish Patent No. PL228483 B1). The reconstruction techniques used in the device enables both morphological and functional imaging. Thanks to innovative approach to construction of diagnostic chamber, CT scanner enables imaging of the whole patient or his or her bigger part, while applying properly long scintillators blocks. It is particularly advantageous in the case of detecting cancer metastases. This solution not only allows the fastest examination of the patient and disease detecting but also reduces the examination costs and shortens the time needed for diagnostics of one person. PET also enables to monitor effects of conducted therapy. PET scanners are invaluable diagnostic tool because of possibility of detecting cancer disease even in their early stages, which enables immediate treatment and choice of proper therapy. However, diagnostic chambers which are presently used consist of the detector ring containing many small inorganic scintillators, which are very expensive. Because of the price diagnostics using positron emission tomography is out of reach in most of the countries in the world.

The aim of the invention described in patent application WO2011/008118 and WO2011/008119 and in publication (P. Moskal et al., "A novel TOF-PET detector based on organic scintillators", Radiotherapy & Oncology 110 (2014) S69) is to lower the costs of the CT scanner significantly by replacing expensive inorganic scintillators by cheap polymeric ones, while improving the quality of imaging thanks to application of innovative method of image reconstruction. General use of this type of detectors would find application also in experiments of particle physics and nuclear physics.

The polymeric scintillators are produced by dissolving scintillating additions in refined liquid monomer and by initiating polymerization reaction. The amount of the first fluorescent addition usually does not exceed 20%, though it is usually 1-2% (N. Zaitseva et al., "Plastic scintillators with effective pulse shape discrimination for neutron and gamma detection". Patent WO2012142365 A3, 2012).

The processes of polymeric scintillators production are different depending on used temperature cycle during polymerization process. Scintillators can be produced by using polymerization initiator or by initiating reaction thermally. The reaction takes place in tight closed containers, the solution with dissolved additions is barbotaged by inert gas to remove oxygen causing yellowing of emerging polymer (A. Bross, K. Mellott i A. Pla-Dalmau, "Extruded plastic scintillator including inorganic powders". U.S. Pat. No. 7,067,079 B2, 2006). In the case of using initiator, the reaction takes place in low temperature of about 50° C., while in the case of lack of initiator, the polymerization reaction is caused by the temperature in the range of 120-200° C. and it is run in properly assorted, optimized time.

2-(4-styrylphenyl)benzoxazole is obtained during quite simple synthesis which does not require great expenses.

For the first time 2-(4-styrylphenyl)benzoxazole was obtained by Adolf Emil Siegrist and his coworkers in 1960 and it was used with the series of similar structures as an optical brightener. The procedure of obtaining it is described in three patents (Ciba Ltd., Patent No. GB941048, 1960; *Chem. Abstr.,* 1964, vol. 61, 5828c; Ciba Ltd. Patent nr CH374361, 1960; *Chem.Abstr.* 1965, vol.62, 697f; Kodak SA, Patent: BE641415, 1962, *Chem. Abstr.,* 1965, vol.63, 3093a). In 1967 Siegriest's review article concerning stilbenyloxazole was published (Siegrist, Adolf E., Preparation of heterocyclic stilbene compounds. Anil synthesis, *Helvetica Chimica Acta,* 50(3), 906-57, 1967). The compound proposed by us was also used as an emitting material in light-emitting diodes OLED (Ko, Chung-Wen; Tao, Yu-Tai; Danel, Andrzej; Krzeminska, Lidia; Tomasik, Piotr Organic Light-Emitting Diodes Based on 2-(Stilbene-4-yl)benzoxazole Derivatives: An Implication on the Emission Mechanism, *Chemistry of Materials,* 13(7) 2441-2446, 2001) or NLO material (Bobrovnikova, Yu. A.; Vernigor, E. M.; Zverev, G. M.; Luk'yanets, E. A.; Martynov, A. D.; Khrolova, O. R., Effective transformation of the second harmonics of a ruby laser into stimulated radiation in the 400-70 mm range of stilbenyloxazole solutions, *Zhurnal Prikladnoi Spektroskopii*, 13(2) 216-19, 1970. Other applications of this compound concern cosmetic and dental application or photographic materials.

The aim of the invention is to propose new composition of the polymeric scintillator suitable for medical diagnostics, especially in production of CT scanners, PET scanners and SPECT scanners.

Unexpectedly, it appears that scintillating characteristics of 2-(4-styrylphenyl)benzoxazole are similar to characteristics of available wavelength shifters and the advantages resulting from easiness of synthesis enables wider application of the substance as the scintillating addition.

The subject of the invention is use of 2-(Stilbene-4-yl) benzoxazole for production of polymeric scintillators, especially as the second fluorescent addition.

The next subject of the invention is polymeric scintillator characterized by containment of 2,5-diphenyloxazole in the amount of from 1% w/w to 10% w/w and 2-(4-styrylphenyl) benzoxazole in the amount of form 0.01% w/w to 0.1% w/w dissolved in organic polymer, while organic polymer is chosen from the group containing polystyrene or polyvinyltoluene. Favourably polymeric scintillator according to the invention contains 2,5-diphenyloxazole in the amount of about 2% w/w. Equally favorably polymeric scintillator according to the invention contains 2-(4-styrylphenyl)benzoxazole in the amount of about 0.03% w/w.

In the favorable realization of the invention 2-(4-styrylphenyl)benzoxazole is used as the second fluorescent addition in polymeric scintillators. It is the substance intermediating in light transmission in the range of UV (330-380 nm) to the range of visible light (above 400 nm). There are a lot of chemical compounds used as wavelength shifters in scintillators and the choice is determined by the preferred range of wavelength and the first luminescent addition, because the emission spectrum has to overlap with the absorption spectrum of the second addition.

The essence of the present invention is connected with application of 2-(4-styrylphenyl)benzoxazole as the second fluorescent addition in polymeric scintillator on the basis of polystyrene or polyvinyltoluene. The task of wavelength shifter is absorption of the energy from the first UV range and emission in the range of visible light. The maximum of the emission of 2-(4-styrylphenyl)benzoxazole is 400 nm. The substance dissolves in both monomers in the range of concentration from several dozen hundredths of percent. The proper choice of the first fluorescent addition assures effective energy transfer in the way: polymer (non-radiative transmission)—first addition (UV)—2-(4-styrylphenyl)benzoxazole (visible light). That leads to receiving high value of luminous efficiency.

Production of polymeric scintillators with addition of 2-(4-styrylphenyl)benzoxazole and application of them in PET scanner allows to lower the costs of cancer diagnostics and monitoring of anticancer therapy.

Figure 2:
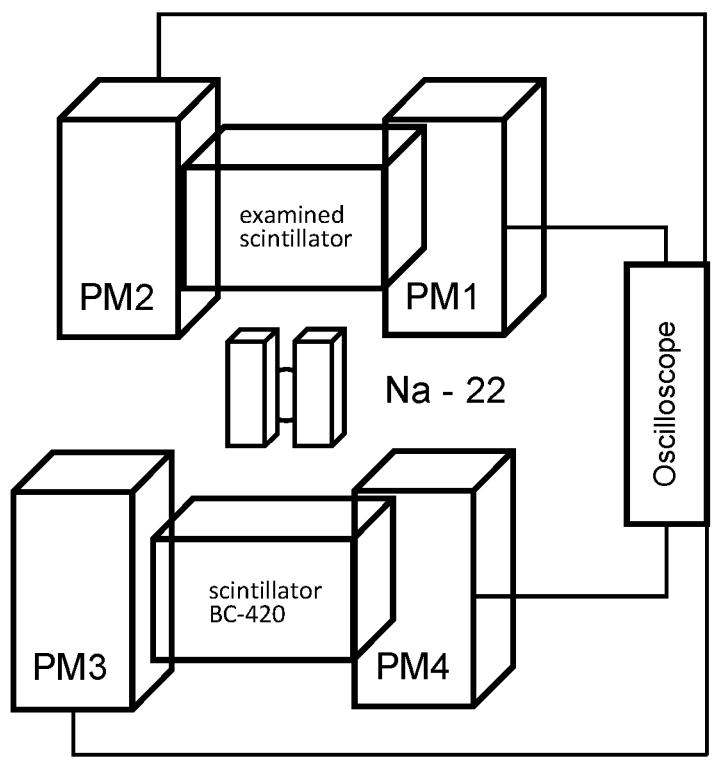

For better explanation of the invention essence the present description is illustrated by the figures, while:

in FIG. 1 there is presented flow chart of experimental system used to determine luminous efficiency of the scintillators;

in FIG. 2 there is presented the scheme of experimental system used to determine time resolution of the scintillators. The abbreviation PM stands for photomultiplier. The source was placed in the lead collimator with space width 1.5 mm.

Moreover, the description contains examples of the produced invention characterized below, which should not be identified with its essence defined above.

EXAMPLE 1

Obtaining Polymeric Scintillator

Synthesis of above mentioned scintillator was the result of dissolving additions: 2,5-diphenyloxazole and 2-(4-styrylphenyl)benzoxazole in monomer in the amount properly: 2% and 0.03% in the relation to mass of the sample and conduction of polymerization reaction of the prepared solution. Examples of the scintillator compositions are presented in the Table 1.

TABLE 1

Composition of example scintillators.

| Polymer | The first addition | The second addition: 2-(4-styrylphenyl)benzoxazole |
|---|---|---|
| Polystyrene | p-terphenyl, 2% w/w | 0.03% w/w |
| Polystyrene | 2,5-diphenyloxazole, 2% w/w | 0.03% w/w |
| Polyvinyltoluene | 2,5-diphenyloxazole, 2% w/w | 0.01% w/w |
| Polyvinyltoluene | 2,5-diphenyloxazole, 2% w/w | 0.02% w/w |
| Polyvinyltoluene | 2,5-diphenyloxazole, 2% w/w | 0.03% w/w |
| Polyvinyltoluene | 2,5-diphenyloxazole, 2% w/w | 0.04% w/w |
| Polyvinyltoluene | 2,5-diphenyloxazole, 2% w/w | 0.05% w/w |

Before the reaction, monomer (styrene, vinyltoluene) was cleaned by granules of activated alumina with 4A molecular sieve. Next, the proper amount of fluorescent additions were dissolved in liquid monomer, the solution was pour into glass ampoule, which was earlier silanized to avoid glass adhesion to polymer and was barbotaged by argon for a few minutes. The ampoule was closed tight in flame of the burner.

Polymerization process was initiated thermally. The temperature cycle used during scintillator production was following: 0.01 h—100° C., 4 h—140° C., 72 h—140° C., 10 h—90° C., 2 h—90° C., 12 h—30° C.

As a result of long synthesis, which lasted about 100 hours homogeneous scintillator was produced with good optical characteristics.

EXAMPLE 2

Optical Characteristics of Polymeric Scintillator According to the Invention

Scintillator obtained according with Example 1. was tested in the experiment described below.

To determine luminous efficiency of the scintillator experimental system presented in FIG. 1 was used. All samples were equally cut and polished, and wrapped with thread tape, with one edge unwrapped which was attached to photomultiplier window with optical gel EJ550. The source of gamma quanta was isotope 137 Cs emitting gamma quanta with energy 622 keV reacting with the scintillator. The measurement was performed for the samples containing 2-(4-styrylphenyl)benzoxazole and for the check standard of scintillators BC-420 from the company Saint Gobain. Using oscilloscope spectrum of signal height ending with Compton edge were registered. On the basis of the edge center luminous efficiency of the scintillator was determined. In the limits of measurement uncertainty it was confirmed that luminous efficiency of the scintillator which is the subject of this patent application does not differ from the luminous efficiency of the scintillator BC-420.

The time resolution was determined of the scintillator containing 2-(4-styrylphenyl)benzoxazole for registration of gamma quanta with energy 511 keV used in PET scanners. In the system presented in FIG. 2 two scintillators wrapped in the Vikuity foil were placed: the one examined and the check standard with the same size (14 mm×14 mm×20 mm). The check standard was the scintillator B-420 from the company Saint-Gobain. The scintillators were exposed in the middle of their length and the source emitting annihilating gamma quanta was isotope 22 Na. The energy of emitting gamma quanta was 511 keV. Using such prepared set the measurement of difference in time between signals from photomultipliers PM1 and PM2 as well as PM3 and PM4 was conducted. In the above mentioned system the time resolution determining interaction time of gamma quantum were really good, on the level of 50 ps. Similar value was received for the commercial scintillator BC-420.

The invention claimed is:

1. A polymeric scintillator, comprising 2,5-diphenyloxazole in the amount from 1% w/w to 10% w/w and 2-(4-styrylphenyl)benzoxazole in the amount from 0.01% w/w to 0.1% w/w dissolved in an organic polymer, wherein the organic polymer is polystyrene or polyvinyltoluene.

2. The polymeric scintillator according to claim 1, wherein said 2,5-diphenyloxazole is present in the amount of about 2% w/w.

3. The polymeric scintillator according to claim 1, wherein said 2-(4-styrylphenyl)benzoxazole is present in the amount of about 0.03% w/w.

* * * * *